US005777171A

United States Patent [19]
Swearengin

[11] Patent Number: 5,777,171
[45] Date of Patent: Jul. 7, 1998

[54] METHOD OF PURIFYING ARYLPHENONES

[76] Inventor: John V. Swearengin, 2012 GAines, El Dorado, Ark. 71730

[21] Appl. No.: 953,558

[22] Filed: Oct. 17, 1997

[51] Int. Cl.[6] .................................................. C07C 45/80
[52] U.S. Cl. .................................................. 568/324
[58] Field of Search .................................................. 568/324

[56] References Cited

U.S. PATENT DOCUMENTS

| 2,752,398 | 6/1956 | Riley | 568/756 |
| 3,526,666 | 9/1970 | Ponder | 568/322 |
| 3,850,988 | 11/1974 | Ruby | 568/324 |
| 4,154,964 | 5/1979 | Balg | 568/757 |
| 5,025,090 | 6/1991 | Barda | 568/33 |

*Primary Examiner*—James H. Reamer
*Attorney, Agent, or Firm*—Joseph A. Strode

[57] ABSTRACT

Hydroxy and alkyloxy benzophenones, also known as arylphenones, are efficiently and economically purified by contacting them with inorganic phosphorous compounds in the presence of a non-polar solvent. Best results are obtained when the arylphenone is then treated with an activated carbon and/or activated clay.

37 Claims, No Drawings

METHOD OF PURIFYING ARYLPHENONES

BACKGROUND OF THE INVENTION

This invention pertains to a novel method of purification of highly colored crude hydroxy and alkyloxy benzophenones (arylphenones) by contacting them with an inorganic phosphorous compound in a non-polar solvent.

DESCRIPTION OF THE PRIOR ART

Arylphenones, such as 2,4-dihydroxy benzophenone, and related substituted benzophenone products are widely used as ultra-violet light absorbers in coating and polymeric compositions, such as polyvinylchloride, polyester, polyacrylate, etc. They are also useful in protection of certain dyes and adhesives against the effects of ultra-violet light.

It is desirable that such products be as light in color as possible in order to not affect the color of the material to which it may be applied. U.S. Pat. Nos. 3,526,666 and 3,850,988 discuss attempts to purify a colored crude product. In particular, good discussions of prior art purification methods can be found in U.S. Pat. No. 3,850,988. However, none of the prior art methods achieve the desired results of purifying and decoloring the crude product without substantial amounts of purifying agents and/or multiple purification attempts. Prior art purifying and decoloring methods therefore tend to be time consuming and expensive, and it is not commercially feasible to purify crude product with particularly high levels of impurities or discoloration to an acceptable level.

Although multiple repetitions may eventually produce a product with acceptable purity, multiple repetitions are time consuming, increase the required quantity of purifying agents, and each repetition typically reduces the eventual yield of purified product by 10–15%.

SUMMARY OF INVENTION

One object of this invention is to provide a method for purification and decolorization of crude arylphenones which contain colorants and/or impurities at a level which previously known methods are not effective in purifying without multiple repetitions.

Another object is to provide a method of purification and decolorization of arylphenones that is more economical and efficient than previously known methods.

A further object of the invention is to provide a method for the purification of arylphenones which comprises contacting the crude arylphenone with phosphoric acid ($H_3PO_4$), phosphorous acid ($H_3PO_3$) or phosphorous pentoxide ($P_2O_5$) in a non-polar solvent.

Further objects and advantages of the invention will become apparent as this disclosure proceeds.

In satisfaction of the foregoing objects and advantages there is provided a method for the purification of arylphenones, which comprises contacting the impure arylphenones with inorganic phosphorous compounds such as phosphoric acid, phosphorous acid or phosphorous pentoxide in the presence of a non-polar solvent. As used in this application, the phrase phosphoric acid is intended to include concentrations ranging from 75% to 115%, and includes the super concentrated form commonly known as poly phosphoric acid. Best results are obtained by further contacting the arylphenone with an activated carbon and/or activated clay, removing the inorganic phosphorous compound and carbon/clay, and then recovering the decolorized/ purified arylphenone from the resultant solution. The amount of inorganic phosphorous compound needed depends on the level of impurities, but will not exceed 15% by weight of the arylphenone, with as little as 2% being adequate.

For best results the ratio of the solvent to the impure arylphenone should be within the range of from 2:1 to 10:1, and the ratio of the carbon/clay to impure arylphenone should be within the range of from 1:100 to 10:100 by weight.

DESCRIPTION OF PREFERRED EMBODIMENTS

According to this invention it has been found that if inorganic phosphorous compounds such as phosphoric acid, phosphorous acid or phosphorous pentoxide are used in the treatment and purification of arylphenones, prior to treatment with activated clays and/or activated carbons, that decolorization and purification is simple, inexpensive, and effective. The quality of the inorganic phosphorous compound only needs to be a good technical grade. Technical grades of 75% to 115% phosphoric acid are acceptable and are desirable due to their commercial availability and low water content. Low water content is desirable because it allows the solution to be mostly water-free with only a small amount of distillation of the non-polar solvent. Applicant has successfully used phosphorous acid and phosphorous pentoxide of 95–97% purity.

The arylphenones to which the present invention is directed may be defined by the following general formula:

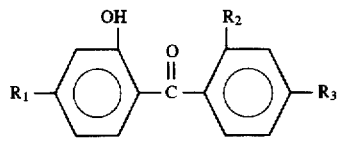

wherein, in the above formula, $R_2$ is H or OH, $R_1$ and $R_3$ are H, OH, or OR, wherein R is $C_1$ to $C_{12}$ alkyl group. The preferred compounds to which the invention is applicable, but not limited, include the following:

2,4-dihydroxybenzophenone 2,2',4-trihydroxybenzophenone 2,2'4,4'-tetrahydroxybenzophenone 2,2'-dihydroxy-4-methoxybenzophenone 2,2'-dihydroxy-4,4'-dimethoxybenzophenone 2-hydroxy-4-methoxybenzophenone 2-hydroxy-4-octyloxybenzophenone 2-hydroxy-4-dodecyloxybenzophenone.

These compounds are well known in the art and can be prepared by any conventional method.

A particularly important feature of the decolorization and purification method of this invention is that it be done in a non-polar solvent. The extraction and/or removal of the phosphorous compound is almost impossible in polar solvents. A non-polar solvent is a compound of the type whose molecules possess no permanent electric moments and primarily are those solvents which either do not ionize, or ionize very weakly in solution.

Preferred solvents of this type which may be used include, but are not limited to, aromatic hydrocarbons, aliphatic hydrocarbons, nitro substituted hydrocarbons, halogenated aromatics, halogenated aliphatics or mixtures thereof. Particularly preferred non-polar solvents are benzene, toluene, chlorobenzene, n-heptane, n-hexane, 1,2-dichloroethane and mixtures thereof.

It has been found that contact time of the arylphenone with the phosphorous compound need only be as long as is needed to distill most of the water from the non-polar solvent at or near atmospheric pressure. Water is contained in the solvent, the crude arylphenone and in some phosphorous or phosphoric acid. All or most of the residual water can be removed using simple distillation at reduced or atmospheric pressure. This is accomplished by heating the mixture to the reflux temperature of the solvent. Experience has shown that as little as ten minutes is adequate, but exposure of several hours is not harmful.

The common rating parameters for measuring the purity of products such as arylphenones are the varnish color scale (VCS) and the Hunter Lab ΔE (ΔE). For most known commercial applications it is generally desirable that the VCS rating be ≦5.0, and that the ΔE rating be ≦60.0. Di-substituted arylphenones are measured at 10% by weight of appropriate clear solvent (such as acetone, methanol, ethanol, toluene, etc.), whereas tri-substituted and tetrasubstituted arylphenones are measured at 5%. Highly pure disubstituted arylphenones are virtually white in color, whereas highly pure tri- and tetra-substituted arylphenones are light yellow.

The following examples are presented to illustrate the method of the present invention. All starting arylphenones were highly colored and contained a high concentration of impurities. All parts are by weight unless otherwise indicated.

EXAMPLE I

A. 55 grams (g) of impure 2,4,-dihydroxybenzophenone with a melting point (m.p.) of 132° C., varnish color scale (VCS) of 9+in a 10% by weight solution of Acetone, and a Hunter Lab ΔE (ΔE) greater than 115, was added to 275 g of toluene under stirring at room temperature.

B. 5.5 g of 85% phosphoric acid was added and heating began. Most material dissolved at 85° C. with a pink viscous oil forming and at 92° C. all material was dissolved except for the pink viscous oil which continued to darken as material was heated to 110° C.

C. Stirring was continued to 10 minutes at 112° C. whereupon the viscous red oil was totally suspended throughout the solution, with the solution being a golden color.

D. All of the above solution was poured into a hot decanting flask whereby all the viscous "red oil" separated to the bottom almost immediately. The upper layer was now a golden clear solution.

E. The bottom layer, consisting of phosphoric acid and impurities, was extracted and discarded.

F. The remaining solution was returned to a stirring vessel and reheated to 100° C. whereupon 3 g of activated clay and 2 g of activated carbon were added. Decolorization occurred almost immediately, but the solution was stirred 30 minutes at 100°–102° C.

G. The solution was then filtered through a hot ceramic filter to remove carbon, clay, residual phosphoric acid, and impurities.

H. The filtered material was cooled under stirring with a light nitrogen pad, and white, almost translucent crystals began to form at 70° C.

I. Material was cooled to room temperature under stirring and nitrogen, then filtered off under vacuum, and formed a damp white cake.

J. The damp white cake was dried at 70° C. and 20 mm vacuum for 4 hours.

K. Yield of white purified material (purified arylphenone) was 47.3 g (86%) with a m.p. of 144.7° C. and a varnish color scale of less than 2 at a 10% by weight solution in Acetone. Hunter Lab was 21. Material is of very high quality and suitable for any known use of such products.

EXAMPLE II

Same as Example I except 6.0 g of 75% phosphoric acid was used instead of the 5.5 g of 85% phosphoric acid. Yield was 46.9 g (85%) of material of virtually the same quality as Example I.

EXAMPLE III

Same as Example I except 5.0 g of polyphosphoric acid was used instead of 85% phosphoric acid. Yield was 47.3 g (86%) of material of virtually the same quality as Example I.

EXAMPLE IV

Same as Example I except no phosphoric acid was used. Resulting material was unacceptable for use, having a m.p. of 142° C., VCS of 8–9 in a 10% by weight solution in Acetone. The ΔE was 94.

EXAMPLE V

Same as Example IV but clay and carbon were increased to 6.0 g each. The m.p. increased to 144.2° C. but material was still highly colored and unacceptable with a VCS of 8+and a ΔE of 88.

EXAMPLE VI

Same as Example I except toluene replaced by chlorobenzene. Results were same as Example I.

EXAMPLE VII

Same as Example I except toluene was replaced by 1,2 dichloroethane. Results were same as Example I.

EXAMPLE VIII

Same as Example I except toluene was replaced by n-butanol. No oily separation and no color improvement occurred after carbon/clay addition. Results were poor and unacceptable.

EXAMPLE IX

Same as Example I except toluene was replaced by methyl isobutyl ketone. Same unacceptable results occurred as in Example VIII.

EXAMPLE X

Same as Example I except toluene was replaced with a 50/50 mixture of Acetone/methanol. Results were unacceptable, just as in Examples VIII and IX.

EXAMPLE XI

Same as Example I except toluene was replaced by perchloroethylene. Similar results as in Example I were obtained, producing excellent quality material.

EXAMPLE XII

Same as Example XI but no phosphoric acid was used. Same unacceptable results as Example IV.

EXAMPLE XIII

Same as Example I but no activated clay was used. Material was acceptable but not as high quality as Example I. M.P. 144.4° C., VCS 3, ΔE 34.

EXAMPLE XIV

Same as Example I but no activated carbon was used. Similar results as Example XIII.

EXAMPLE XV

Same as Example I except 2,4-dihydroxybenzophenone was replaced with a very crude 2,2'-dihydroxy-4, methoxybenzophenone having a m.p. of 58° C., a VCS color of 9+, and a ΔE of 120+.

Toluene was also replaced with mineral spirits due to this benzophenone's high solubility in toluene.

Results obtained were similar to results of Example I. M.P. of 71° C., VCS of 2.0–2.5 and ΔE of 32.

EXAMPLE XVI

Same as Example XV except mineral spirits was replaced by n-heptane. Similar results as in Example XV.

EXAMPLE XVII

Same as Example XV except mineral spirits was replaced by ethanol. No separation was obtained and very little decolorization. Results were poor and unacceptable.

EXAMPLE XVIII

Same as Example I except 2,4-dihydroxybenzophenone was replaced by crude 2,2'dihydroxy-4, 4'dimethoxybenzophenone with a m.p. of 126° C., VCS of 8, and ΔE of 92. A good quality material with a m.p. of 138° C., VCS 3.0–3.5 and ΔE of 39 was produced.

EXAMPLE XIX

Same as Example XVI except 2,2'dihydroxy-4- methoxybenzophenone was replaced by crude 2-hydroxy-4- methoxybenzophenone. Excellent results were obtained as in Example XVI.

EXAMPLE XX

Same as Example XIX except 2-hydroxy-4-methoxybenzophenone was replaced by 2-hydroxy-4-octyloxybenzophenone. Similar results as in Example XIX.

EXAMPLE XXI

Same as Example XX but n-heptane was replaced by isopropanol. Very little improvement in color. Results poor and unacceptable.

EXAMPLE XXII

Same as Example I except phosphoric acid and impurities were not extracted prior to addition of clay and carbon. Although slower to filter off the clay, carbon, phosphoric acid, and impurities, an acceptable product was obtained with m.p. of 144.20° C., VCS of 3, and ΔE of 37.

EXAMPLE XXIII

Same as Example I except no activated clay or activated carbon was used after phosphoric acid and impurities were extracted. Although not acceptable, material has more improvement in color than when only activated clay and activated carbon were used without phosphoric acid or other phosphorous compound. Material has a m.p. of 142 with a VCS of 6–7, and ΔE of 69.

EXAMPLE XXIV

Same as Example I except the 5.5 g of 85% phosphoric acid ($H_3PO_4$) was replaced with 1.5 g of phosphorous pentoxide ($P_2O_5$). Yield was 46.7 g of excellent quality material having a m.p. of 145° C., VCS of 1.5 and ΔE of 19.0.

EXAMPLE XXV

Same as Example XXIV except no clay or carbon were used. Resulting material was of acceptable quality, having a m.p. of 144° C. VCS of 5.0 and ΔE of 56.3.

EXAMPLE XXVI

Same as Example XXIV except 2, 4, -dihydroxybenzophenone was replaced with 2,2 dihydroxy-4, 4 dimethoxy benzophenone. Resulting material was of acceptable quality, having a m.p. of 140° C., VCS of 3.0, and ΔE of 44.0.

EXAMPLE XXVII

Same as Example XXIV except 2, 4, -dihydroxybenzophenone was replaced with 2, 2, 4 trihydroxybenzophenone. Resulting material was of quality equal to or better than Example XXVI.

EXAMPLE XXVIII

Same as Example XXIV except clay and carbon were reduced to 1.0 g each. Yield was 47.5 g of excellent quality material, having a m.p. of 145° C., VCS of 2 and ΔE of 23.1.

EXAMPLE XXIX

Same as Example XXIV except 5.5 g of ortho phosphoric acid ($H_3PO_4$) was replaced with 1.5 g of phosphorous acid ($H_3PO_3$). Quality of resulting material was almost identical to Example XXIV, having a m.p. of 145° C., VCS of 1.5 and ΔE of 20.1.

EXAMPLE XXX

Same as Example XXIX except no clay or carbon was used. Resulting material was of acceptable quality, having a m.p. of 144° C., VCS between 4 and 5, and ΔE of 54.

EXAMPLE XXXI

Same as Example XXX except $H_3PO_3$ was increased to 2.5 g. Resulting material was of slightly better quality, having a m.p. of 144 C, VCS of 4 and ΔΔE of 48.1.

EXAMPLE XXXII

Same as Example XXIX except 2, 4-dihydroxybenzophenone was replaced with 2, 2 dihydroxy-4 methoxybenzophenone. Excellent material was produced having a melting point of 720° C., VCS of 2.5 and ΔE of 29.8.

EXAMPLE XXXIII

Same as Example XXIX except 2, 4 dihydroxy benzophenone replaced with 2, 2 dihydroxy-4, 4 dimethoxybenzophenone. Produced excellent material with m.p. of 140° C., VCS of 3.0 and ΔE of 43.3.

As can be seen from the foregoing examples the novel use of phosphoric acid, phosphorous acid, or phosphorous pentoxide is the key to obtaining a high level or purity. When used without either activated clay or carbon, the result is better than the existing conventional process of using only clay and/or carbon as the purifying agent. When phosphoric acid, phosphorous acid or phosphorous pentoxide are used prior to treatment with activated clay and/or carbon, vastly superior results are obtained.

I claim:

1. A method for the decolorization and purification of an impure arylphenone of the following formula:

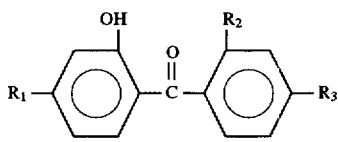

wherein $R_2$ is H or OH, $R_1$, and $R_3$ are H, OH or OR, and R is a $C_1$ to $C_{12}$ alkyl group, comprising contacting the impure arylphenone with a non-polar solvent and an inorganic phosphorous compound selected from the group of phosphoric acid, phosphorous acid, or phosphorous pentoxide.

2. The method of claim 1 further comprising the step of contacting the impure arylphenone with activated carbon.

3. The method of claim 1 further comprising the step of contacting the impure arylphenone with activated clay.

4. The method of claim 1 further comprising the step of contacting the impure arylphenone with a combination of activated clay and activated carbon.

5. A method for the decolorization and purification of an impure arylphenone of the following formula:

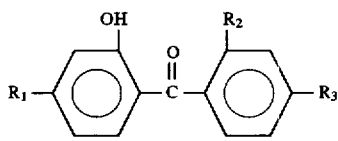

wherein $R_2$ is H or OH, $R_1$, and $R_3$ are H, OH or OR, and R is a $C_1$ to $C_{12}$ alkyl group, comprising:
  (a) mixing a non-polar solvent with the impure arylphenone;
  (b) adding an organic phosphorous compound selected from the group of phosphoric acid, phosphorous acid and phosphorous pentoxide and heating and stirring the mixture of the non-polar solvent, impure arylphenone and phosphorous compound;
  (c) stopping heating and stirring to allow the phosphorous compound and impurities to settle to the bottom;
  (d) separating the settled phosphorous compound and impurities to leave a remaining mixture of purified arylphenone and non-polar solvent;
  (e) cooling said remaining mixture until the purified arylphenone crystalizes;
  (f) filtering said remaining mixture to remove the purified arylphenone;
  (g) drying the purified arylphenone.

6. The method of claim 5 wherein the ratio of the non-polar solvent to the impure arylphenone is within the range of from 2:1 to 10:1 by weight.

7. The method of claim 5 wherein the ratio of the phosphorous compound to the impure arylphenone is within the range of from 2:100 to 15:100 by weight.

8. The method of claim 5 wherein the ratio of the phosphorous compound to the impure arylphenone is within the range of from 2:100 to 15:100 by weight, and the ratio of the non-polar solvent to the impure arylphenone is within the range of from 2:1 to 10:1 by weight.

9. The method of claim 5 where the mixture of non-polar solvent, impure arylphenone and phosphorous compound is heated to the reflux temperature of the solvent for at least ten minutes while stirring.

10. The method of claim 5 where the mixture of non-polar solvent, impure arylphenone and phosphorous compound is heated to the reflux temperature of the solvent for at least ten minutes while stirring, and wherein the ratio of the non-polar solvent to the impure arylphenone is within the range of from 2:1 to 10:1 by weight.

11. The method of claim 5 where the mixture of non-polar solvent, impure arylphenone and phosphorous compound is heated to the reflux temperature of the solvent for at least ten minutes while stirring, and the ratio of the phosphorous compound to the impure arylphenone is within the range of from 2:100 to 15:100 by weight.

12. The method of claim 5 where the mixture of non-polar solvent, impure arylphenone and phosphorous compound is heated to the reflux temperature of the solvent for at least ten minutes while stirring, and wherein the ratio of the non-polar solvent to the impure arylphenone is within the range of from 2:1 to 10:1 by weight, and the ratio of the phosphorous compound to the impure arylphenone is within the range of 2:100 to 15:100 by weight.

13. A method for the decolorization and purification of an impure arylphenone of the following formula:

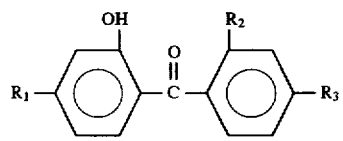

wherein $R_2$ is H or OH, $R_1$ and $R_3$ are H, OH or OR, and R is a $C_1$ to $C_{12}$ alkyl group, comprising:
  (a) mixing a non-polar solvent with the impure arylphenone;
  (b) adding an inorganic phosphorous compound selected from the group of phosphoric acid, phosphorous acid, and phosphous pentoxide and heating while continuing to stir the mixture of non-polar solvent, impure arylphenone and phosphorous compound;
  (c) stopping heating and stirring to allow all but a residual amount of the phosphorous compound and impurities to settle to the bottom;
  (d) separating the settled phosphorous compound and impurities, leaving a remaining mixture of arylphenone, non-polar solvent, and residual phosphorous compound and residual impurities;
  (e) reheating said remaining mixture and adding either activated clay, activated carbon or a combination thereof to further purify the arylphenone;
  (f) removing the carbon and/or clay, the residual phosphorous compound and the residual impurities to form a damp cake of purified arylphenone; and
  (g) drying the purified arylphenone.

14. The method of claim 13 wherein the ratio of the non-polar solvent to the impure arylphenone is within the range of from 2:1 to 10:1 by weight.

15. The method of claim 13 wherein the ratio of the phosphorous compound to the impure arylphenone is within the range of from 2:100 to 15:100 by weight.

16. The method of claim 13 wherein the ratio of the phosphorous compound to the impure arylphenone is within the range of from 2:100 to 15:100 by weight, and the ratio of the non-polar solvent to the impure arylphenone is within the range of from 2:1 to 10:1 by weight.

17. The method of claim 13 where the mixture of non-polar solvent, impure arylphenone and phosphorous compound is heated to the reflux temperature of the solvent for at least ten minutes while stirring.

18. The method of claim 13 where the mixture of non-polar solvent, impure arylphenone and phosphorous compound is heated to the reflux temperature of the solvent for at least ten minutes while stirring, and wherein the ratio of the non-polar solvent to the impure arylphenone is within the range of from 2:1 to 10:1 by weight.

19. The method of claim 13 where the mixture of non-polar solvent, impure arylphenone and phosphorous compound is heated to the reflux temperature of the solvent for at least ten minutes while stirring, and wherein the ratio of the phosphorous compound to the impure arylphenone is within the range of from 2:100 to 15:100 by weight.

20. The method of claim 13 where the mixture of non-polar solvent, impure arylphenone and phosphorous compound is heated to the reflux temperature of the solvent for at least ten minutes while stirring, and wherein the ratio of the phosphorous compound to the impure arylphenone is within the range of from 2:100 to 15:100 by weight and the ratio of the non-polar solvent to the impure arylphenone is within the range of from 2:1 to 10:1 by weight.

21. The method of claim 13 wherein the ratio of the activated clay, activated carbon or combination thereof to the impure arylphenone is within the range of from 1:100 to 10:100 by weight.

22. The method of claim 13 wherein the ratio of the activated clay, activated carbon or combination thereof to the impure arylphenone is within the range of from 1:100 to 10:100 by weight, and the ratio of the non-polar solvent to the impure arylphenone is within the range of from 2:1 to 10:1 by weight.

23. The method of claim 13 wherein the ratio of the activated clay, activated carbon or combination thereof to the impure arylphenone is within the range of from 1:100 to 10:100 by weight, and the ratio of the phosphorous compound to the impure arylphenone is within the range of from 2:100 to 15:100 by weight.

24. The method of claim 13 wherein the ratio of the activated clay, activated carbon or combination thereof to the impure arylphenone is within the range of from 1:100 to 10:100 by weight, the ratio of the non-polar solvent to the impure arylphenone is within the range of from 2:1 to 10:1 by weight, and the ratio of the phosphorous compound to the impure arylphenone is within the range of from 2:100 to 15:100 by weight.

25. The method of claim 13 wherein the ratio of the activated clay, activated carbon or combination thereof to the impure arylphenone is within the range of from 1:100 to 10:100 by weight, and the mixture of non-polar solvent, impure arylphenone and phosphorous compound is heated to the reflux temperature of the solvent for at least ten minutes while stirring.

26. The method of claim 13 wherein the ratio of the activated clay, activated carbon or mixture thereof to the impure arylphenone is within the range of from 1:100 to 10:100 by weight, the ratio of the non-polar solvent to the impure arylphenone is within the range of from 2:1 to 10:1 by weight and the mixture of non-polar solvent, impure arylphenone and phosphorous compound is heated to the reflux temperature of the solvent for at least ten minutes while stirring.

27. The method of claim 13 wherein the ratio of the activated clay, activated carbon or combination thereof to the impure arylphenone is within the range of from 1:100 to 10:100 by weight, the ratio of the phosphoric compound to the impure arylphenone is within the range of from 2:100 to 15:100 by weight and the mixture of non-polar solvent, impure arylphenone and phosphorous compound is heated to the reflux temperature of the solvent for at least ten minutes while stirring.

28. The method of claim 13 wherein the ratio of the activated clay, activated carbon or combination thereof to the impure arylphenone is within the range of from 1:100 to 10:100 by weight, the ratio of the phosphorous compound to the impure arylphenone is within the range of from 2:100 to 15:100 by weight, the ratio of the non-polar solvent to the impure arylphenone is within the range of from 2:1 to 10:1 by weight, and the mixture of non-polar solvent, impure arylphenone and ortho phosphorous compound is heated to the reflux temperature of the solvent for at least ten minutes while stirring.

29. A method for the decolorization and purification of an impure arylphenone of the following formula:

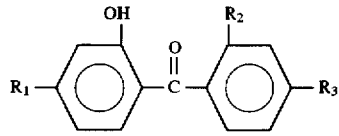

wherein $R_2$ is H or OH, $R_1$ and $R_3$ are H, OH or OR, and R is a $C_1$ to $C_{12}$ alkyl group, comprising:
  (a) mixing a non-polar solvent with the impure arylphenone;
  (b) adding a phosphorous compound selected from among the group of phosphoric acid, phosphorous acid and phosphorous pentoxide and heating the mixture of non-polar solvent, impure arylphenone and phosphorous compound while stirring;
  (c) stopping heating and stirring until the phosphorous compound and impurities settle to the bottom;
  (d) separating the phosphorous compound and impurities from the remaining mixture;
  (e) reheating said remaining mixture and adding a combination of activated clay and activated carbon and stirring to form a second mixture;
  (f) filtering said second mixture in a first filtering phase consisting of filtering through a hot ceramic filter to form a first phase filtered material;
  (g) cooling said first phase filtered material to room temperature while stirring under nitrogen;
  (h) further filtering the first phase filtered material in a second filtering phase under vacuum to form a damp cake of purified arylphenone; and
  (i) drying the damp cake of purified arylphenone.

30. The method of claim 29 wherein the ratio by weight of the non-polar solvent to the impure arylphenone is within the limits of from 2:1 to 10:1, the ratio of the phosphorous compound to the impure arylphenone is within the limits of from 2:100 to 15:100, and the ratio of the combination of activated carbon and activated clay to the impure arylphenone is within the limits of from 1:100 to 10:100.

31. The method of claim 29 wherein the arylphenone is selected from a group including:

2,4-dihydroxybenzophenone;
2,2',4-trihydroxybenzophenone;
2,2',4,4'-tetrahydroxybenzophenone;
2,2'-dihydroxy-4-methoxybenzophenone;
2,2'-dihydroxy-4,4'-dimethoxybenzophenone;
2-hydroxy-4-methoxybenzophenone;
2-hydroxy-4-octyloxybenzophenone; and
2-hydroxy-4-dodecyloxybenzophenone.

32. The method of claim 29 wherein the non-polar solvent is selected from a group including aromatic hydrocarbons; aliphatic hydrocarbons; nitro substituted hydrocarbons; halogenated aromatics; halogenated aliphatics; and mixtures thereof.

33. The method of claim 29 wherein the non-polar solvent is selected from a group including benzene; toluene; chlorobenzene; n-heptane; n-hexane; 1,2-dichloroethane; and mixtures thereof.

34. The method of claim 29 wherein said mixture and said remaining mixture are both heated to the reflux temperature of the solvent.

35. The method of claim 29 wherein the phosphorous compound is phosphoric acid in a concentration of from 75% to 115%.

36. A method for the decolorization and purification of an impure arylphenone of the following formula:

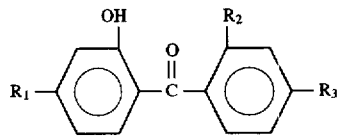

wherein $R_2$ is H or OH, $R_1$ and $R_3$ are H, OH or OR, and R is a $C_1$ to $C_{12}$ alkyl group, comprising:

(a) mixing a non-polar solvent with the impure arylphenone;

(b) adding an inorganic phosphorous compound and either activated clay, activated carbon or a combination of activated clay and carbon to form a mixture;

(c) heating the mixture while continuing to stir;

(d) stopping heating and stirring to allow the phosphorous compound, impurities, carbon and clay to settle to the bottom;

(e) separating the settled phosphorous compound, impurities, carbon and clay from the remaining mixture;

(f) cooling said remaining mixture until the purified arylphenone crystalizes;

(g) filtering to remove the purified arylphenone;

(h) drying the purified arylphenone.

37. The method of claim 36 wherein the ratio of the activated clay, activated carbon or combination thereof to the impure arylphenone is within the range of from 1:100 to 10:100 by weight, the ratio of the non-polar solvent to the impure arylphenone is within the range of from 2:1 to 10:1 by weight, and the ratio of the phosphorous compound to the impure arylphenone is within the range of from 2:100 to 15:100 by weight.

* * * * *